United States Patent
Crawford et al.

[11] Patent Number: 5,216,601
[45] Date of Patent: Jun. 1, 1993

[54] METHOD FOR FAN BEAM HELICAL SCANNING USING REBINNING

[75] Inventors: Carl R. Crawford, Milwaukee; Kevin F. King, New Berlin, both of Wis.

[73] Assignee: General Electric Company, Milwaukee, Wis.

[21] Appl. No.: 440,530

[22] Filed: Nov. 22, 1989

[51] Int. Cl.$^5$ .............................................. G06F 15/00
[52] U.S. Cl. ........................... 364/413.16; 364/413.18
[58] Field of Search ...................... 364/413.16, 413.17, 364/413.18, 413.19; 378/4, 20, 14

[56] References Cited

U.S. PATENT DOCUMENTS

| | | | |
|---|---|---|---|
| 4,284,896 | 8/1981 | Stonestrom | 250/413.14 |
| 4,630,202 | 12/1986 | Mori | 364/413.14 |
| 4,789,929 | 12/1988 | Nishimura et al. | 364/413.15 |
| 5,073,911 | 12/1991 | Ozaki et al. | 364/413.21 |

Primary Examiner—Roy N. Envall, Jr.
Assistant Examiner—Xuong Chung
Attorney, Agent, or Firm—Quarles & Brady

[57] ABSTRACT

A method of reducing image artifacts in images acquired with fan beam, helical scanning, tomographic imaging systems rebins the fan beam data into parallel beam projection sets. Data is spliced from first areas of the parallel beam projection data to second areas to create a set of $2\pi$ radians of complete projection data. The $2\pi$ of projection data is divided into half scans which are interpolated and extrapolated to produce a new projection set at the slice plane with reduced helical offset error. A feathering function is used to blend the discontinuities in the interpolation and extrapolation weights to prevent streak image artifacts.

5 Claims, 5 Drawing Sheets

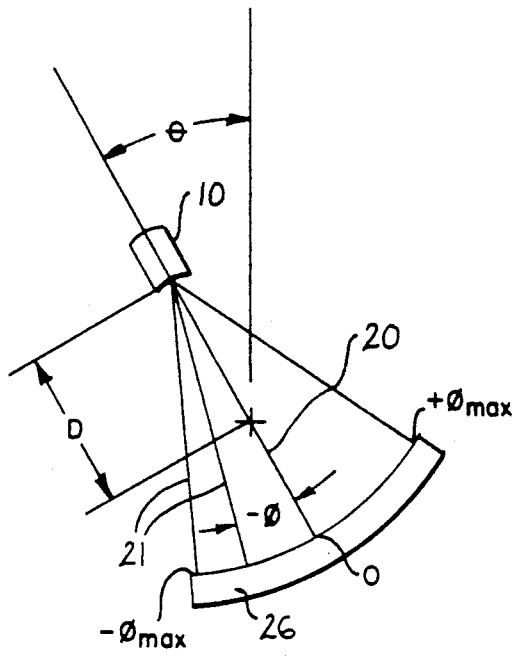
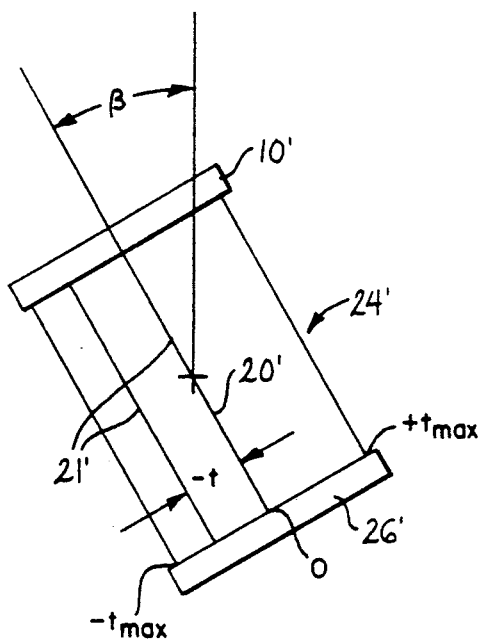
FIG. 4a
FIG. 4b
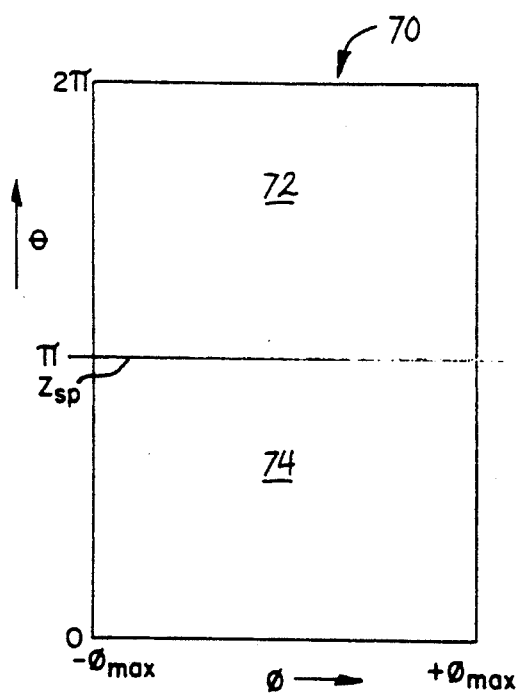
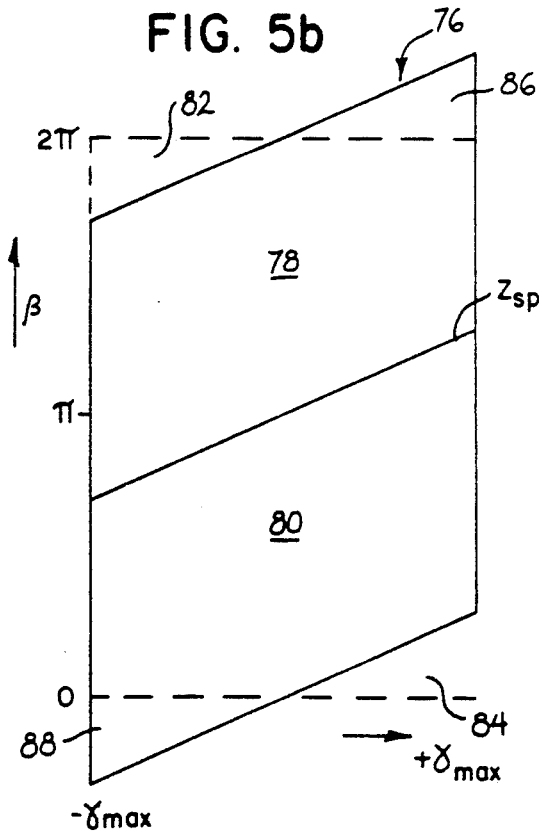
FIG. 5a
FIG. 5b

METHOD FOR FAN BEAM HELICAL SCANNING USING REBINNING

BACKGROUND OF THE INVENTION

This invention relates to computed tomography using helical scanning. More specifically, the invention relates to an image reconstruction method for reducing image artifacts that result from acquiring tomographic projection data in a helical scan.

In a fan beam x-ray computed tomography system, an x-ray source is collimated to form a fan beam with a defined fan beam angle. The fan beam is orientated to lie within the x-y plane of a Cartesian coordinate system, termed the "imaging plane", and to be transmitted through an imaged object to an x-ray detector array orientated within the imaging plane. The detector array is comprised of detector elements which each measure the intensity of transmitted radiation along a ray projected from the x-ray source to that particular detector element. The detector elements can be organized along an arc each to intercept x-rays from the x-ray source along a different ray of the fan beam. The intensity of the transmitted radiation is dependent on the attenuation of the x-ray beam along the ray by the imaged object.

The x-ray source and detector array may be rotated on a gantry within the imaging plane, around the imaged object, so that the fan beam intercepts the imaged object at different angles. At each angle, a projection is acquired comprised of the intensity signals from each of the detector elements. The gantry is then rotated to a new angle and the process is repeated to collect a number of projections at different angles to form a tomographic projection set.

The acquired tomographic projection set is typically stored in numerical form for computer processing to "reconstruct" a slice image according reconstruction algorithms known in the art. The reconstructed slice images may be displayed on a conventional CRT tube or may be converted to a film record by means of a computer controlled camera.

A typical computed tomographic study entails the imaging of a series of slices of an imaged object with the slices displaced incrementally along a z-axis perpendicular to the x and y axes, so as to provide a third spatial dimension of information. A radiologist may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, additional slices are required in the z-dimension. The time and expense of a tomographic study increases with the number of slices required. Also, longer scan times increase the discomfort to the patient who must remain nearly motionless to preserve the fidelity of the tomographic reconstructions. Accordingly, there is considerable interest in reducing the time required to obtain a slice series.

The time required to collect the data for a series of slices depends in part on four components: a) the time required to accelerate the gantry to scanning speed, b) the time required to obtain a complete tomographic projection set, c) the time required to decelerate the gantry and d) the time required to reposition the patient in the z-axis for the next slice. Reducing the time required to obtain a full slice series may be accomplished by reducing the time required to complete any of these four steps.

The time required for acceleration and deceleration of the gantry may be avoided in tomographic systems that use slip rings rather than cables to communicate with the gantry. The slip rings permit continuous rotation of the gantry. Hereafter, it will be assumed that the CT systems discussed are equipped with slip rings or the equivalent to permit continuous rotation of over 360°.

The time required to acquire the tomographic data set is more difficult to reduce. Present CT scanners require on the order of one to two seconds to acquire the projection set for one slice. This scan time may be reduced by rotating the gantry at a faster speed. A higher gantry speed, in general, will reduce the signal-to-noise ratio of the acquired data by the square root of the factor of rotational rate increase. This may be overcome to some extent in transmission tomography devices by increasing the radiation output of the x-ray tube, but is subject to the power limits of such devices.

A reduction in patient repositioning time may be accomplished by translating the patient in the z-axis synchronously with the rotation of the gantry. The combination of constant patient translation along the z-axis during the rotation of the gantry and acquisition of projection data has been termed "helical scanning" and refers to the apparent path of a point on the gantry with respect to a reference point on the imaged body. As used herein, "helical scanning" shall refer generally to the use of continuous translation of the patient or imaged object during the acquisition of tomographic imaging data, and "constant z-axis scanning" shall refer to the acquisition of the tomographic data set without translation of the patient or imaged object during the acquisition period.

Continuous translation of the imaged object during scanning shortens the total scanning time required for the acquisition of a given number of slices by eliminating the length of time normally required for repositioning the patient between scans. However, helical scanning introduces certain errors with regard to the data in the acquired tomographic projection sets. The mathematics of tomographic reconstruction assumes that the tomographic projection set is acquired along a constant z-axis slice plane. The helical scan path clearly deviates from this condition and this deviation results in image artifacts in the reconstructed slice image if there is any significant change in the object in the z-axis. The severity of the image artifacts depends generally on the "helix offset" in the projection data, measured as the difference between the table locations of the scanned data and the z axis value of the desired slice plane. Errors resulting from helical scanning will be referred to collectively as "skew" errors.

Several methods have been used to reduce skew errors in helical scanning. A first approach disclosed in copending U.S. patent application Ser. No. 07/371,332 filed Sep. 3, 1991 entitled "Method for Reducing Skew Image Artifacts in Helical Projection Imaging" and assigned to the same assignee as the present invention, uses non-uniform table motion to concentrate the helically acquired projections near the slice plane while limiting the accelerative forces on the patient.

In co-pending U.S. patent application Ser. No. 07/430,372 filed Nov. 2, 1989 entitled "Computerized Tomographic Image Reconstruction Method for Helical Scanning", and assigned to the same assignee as the present invention, skew artifacts are reduced by interpolating between two half scans of data each requiring only 180° plus the fan beam angle of gantry rotation. The half scans require less gantry rotation and hence less table movement, thereby reducing the overall helical offset of the projection data.

In a third approach described in co-pending U.S. patent application Ser. No. 07/435,980 filed Nov. 13, 1989 entitled "Extrapolative Reconstruction Method for Helical Scanning", and assigned to the same assignee as the present invention, skew artifacts are reduced by interpolating and extrapolating between two partial projection sets of only 180° of gantry rotation. The two partial projection sets require even less gantry rotation than the above half scan approach and, thereby further reduce the overall helical offset of the projection data.

SUMMARY OF THE INVENTION

It is understood in the art, that a tomographic image may be prepared from projection data acquired over less than 360° of gantry rotation. Generally, this result arises from the equivalence in attenuation of certain rays in projections acquired at gantry angles 180° apart. This method of reconstructing a tomographic image is termed "half scan" reconstruction. The weighting and reconstruction of images from a half scan data set are discussed in detail in "Optimal Short Scan Convolution Reconstruction for Fanbeam CT", Dennis L. Parker, Medical Physics 9(2) March/April, 1982.

The present invention reduces skew artifacts in helically acquired data by interpolating and extrapolating a projection set with reduced helical offset from two parallel beam half scans acquired near the slice plane. The half scans are created from fan beam projections acquired over only $2\pi$ of gantry rotation by means of a splicing procedure.

Specifically, fan beam projection data is acquired during $2\pi$ of gantry rotation and rebinned into corresponding parallel beam projection sets. Two half scans are divided out of the rebinned parallel beam projections set. The data from these half scans is spliced so as to create a full $2\pi$ of parallel beam projections. The half scans are weighted to permit interpolation and extrapolation to the slice plane and then reconstructed to form an image.

It is one object of the invention to permit the acquisition of projection data for a single slice image over a shorter z-axis distance. The splicing process allows the parallel beam half scans to be acquired in 360°. For a given scan pitch, the use of two parallel beam half scans acquired in 360° rather than two full scans acquired in 720°, requires less z-axis travel in a helical scan. This in turn concentrates the projections acquired at points closer to the slice plane and thus improves the accuracy of the interpolation and extrapolation and decreases partial volume artifacts.

It is another object of the invention to permit the acquisition of projection data for a single slice image over a shorter time period. Image artifacts may result from patient motion during the acquisition of the projection data of a tomographic projection set. For a given gantry speed, the use of parallel beam half scans acquired in only 360° of gantry rotation permits the reconstruction of images that are less susceptible to motion artifacts.

It is another object of the invention to improve the efficiency of the half scanning process. By splicing data acquired in 360° of gantry rotation to form the two parallel beam half scans, the total x-ray exposure to the patient may be reduced.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 4(a) is a diagram showing the geometry of an x-ray fan beam CT apparatus and the relationship of the variables $\theta$ and $\phi$ defining each data element of a fan beam projection set;

FIG. 4(b) is a diagram showing the geometry of an x-ray parallel beam CT apparatus and the relationship of the variables $\beta$ and t defining each data element of a parallel beam projection set;

FIG. 5(a) is a graphical representation of the arguments $\theta$ and $\phi$ associated with the projection data of a fan beam projection set acquired in a helical scan with the CT apparatus of FIG. 1;

FIG. 5(b) is a graphical representation of the arguments $\beta$ and $\gamma$ associated with the projection data of a parallel beam projection set produced by rebinning the fan beam projection set of FIG. 5(a);

DETAILED DESCRIPTION OF THE PREFERRED EMBODIMENT

Figure 1:
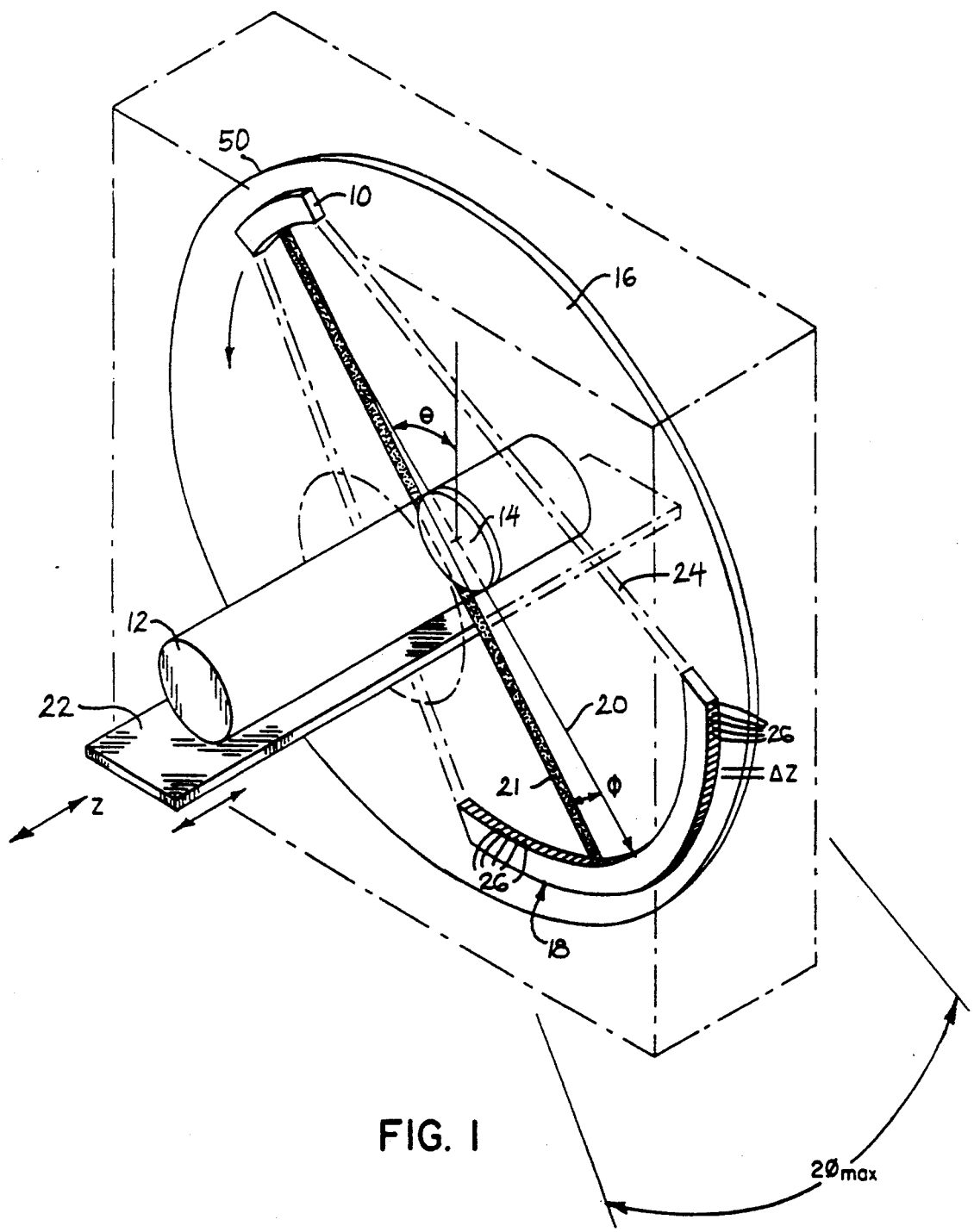
FIG. 1 is a pictorial representation of a CT apparatus including gantry, table and imaged object, and showing the relative angles and axes associated therewith.

Referring to FIG. 1, a CT gantry 16, representative of a "third generation" CT scanner includes an x-ray source 10 oriented to project a fan beam of x-rays 24 through imaged object 12 to detector array 18. The fan beam 24 is directed along an x-y plane of a Cartesian coordinate system, the "imaging plane", and subtends a "fan angle" measured along the imaging plane. The detector array 18 is comprised of a number of detector elements 26 which together receive and detect a value proportional to the magnitude of a projected image resulting from the transmission of x-rays through the imaged object 12.

The gantry 16 is coupled to the gantry associated control modules 48, shown in FIG. 3 and to be described below, by means of slip rings 50 and is therefore free to rotate continuously through angles greater than 360° to acquire projection data.

The imaged object 12 rests on table 22 which is radiotranslucent so as not to interfere with the imaging process.

Table 22 may be controlled so that its upper surface translates along the z axis perpendicular to the x-y imaging plane, by moving the slice plane 14 defined with respect to the imaged object 12 across the imaging plane swept by the fan beam 24. For simplicity, it will be assumed henceforth that the table 22 moves at a constant velocity and therefore that the z axis position of the table 22 is proportional to the angular position $\theta$ of the gantry 16. Accordingly, the tomographic projections acquired may be defined either in terms of z or $\theta$.

Figure 2A:
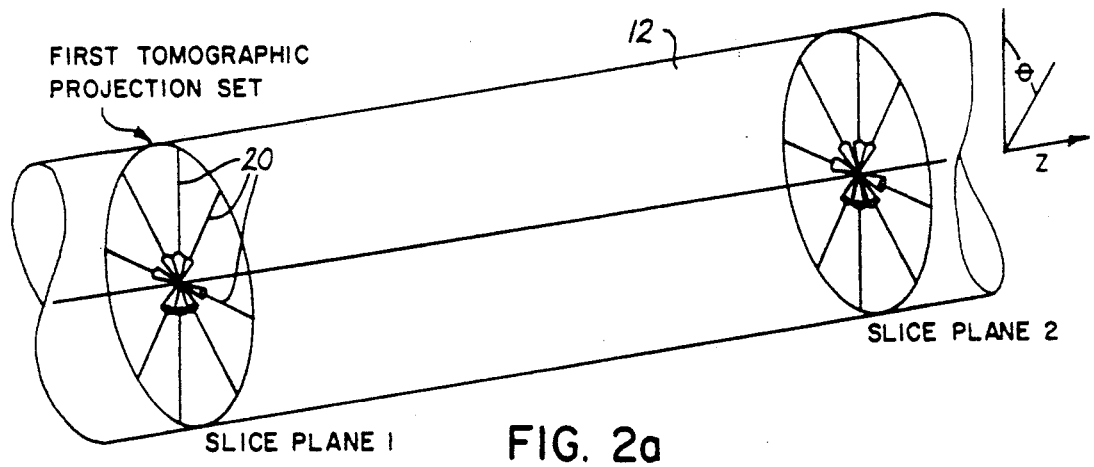
FIG. 2(a) and 2(b) are schematic illustrations of the imaged object of FIG. 1 showing the relative orientation of the gantry and imaging plane with respect to the imaged object for constant z axis scanning and helical scanning respectively. The pitch of the helical scanning is exaggerated for clarity.
Figure 2B:
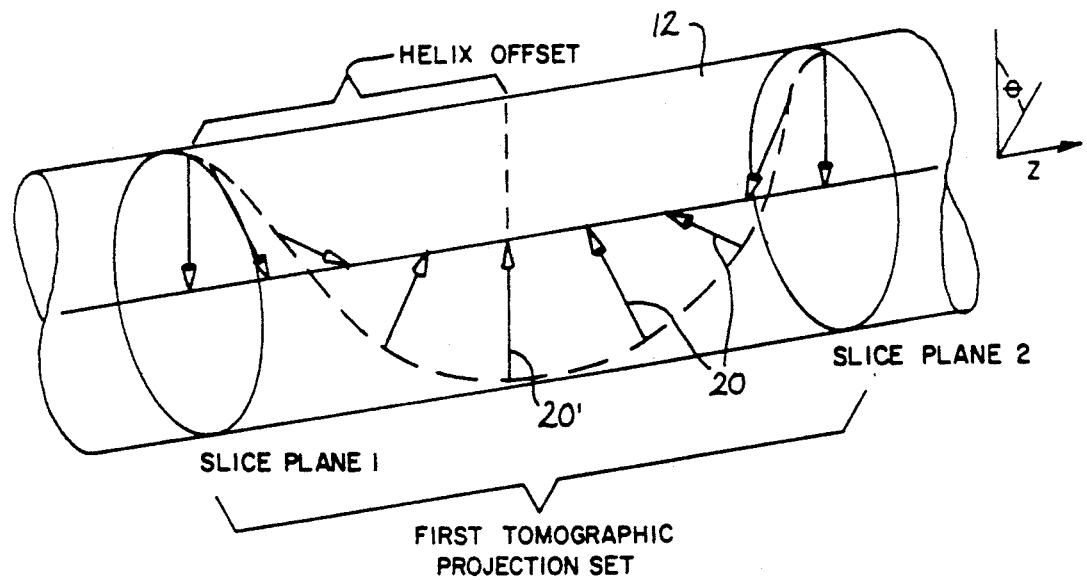

Referring to FIGS. 2(a) and 2(b), the angular position of the gantry and the z-axis position of the imaging plane with respect to the imaged object is shown by projection arrows 20 for a constant z-axis scan and a helical scan, respectively. In the constant z-axis scan, shown in FIG. 2(a) each tomographic projection set is acquired at a constant z-axis position and the imaged object is moved along the z-axis to the next slice plane between such acquisitions.

This differs from the helical scan in FIG. 2(b) where the z-axis position of the imaged object with respect to the imaging plane changes constantly during the acquisition of each tomographic projection set. Accordingly, arrows 20 trace a helix within the imaged object along the z-axis. The pitch of the helix will be referred to as the scanning pitch.

Figure 3:
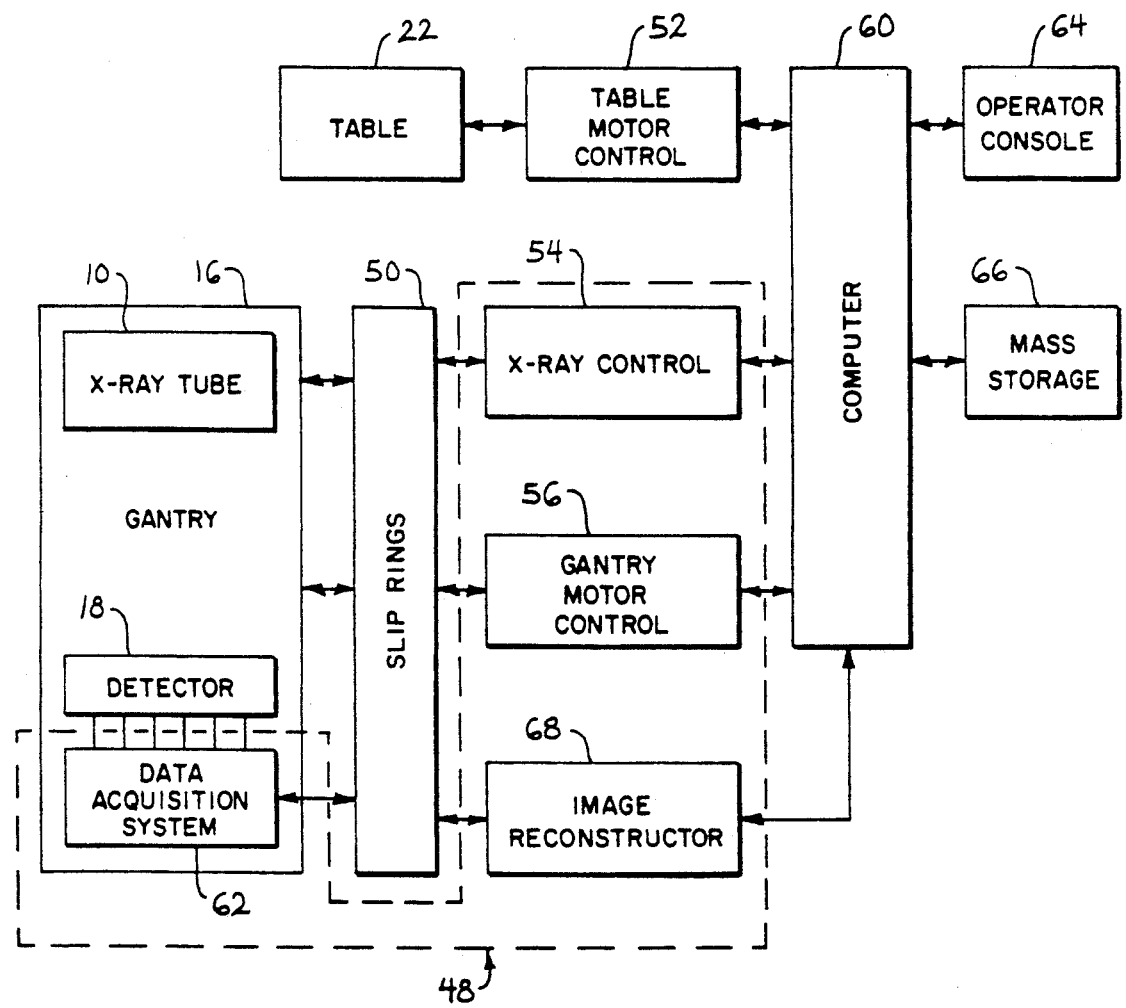
FIG. 3 is a block diagram of a CT control system that may be used with the CT apparatus of FIG. 1, and that is useful for practicing the present invention.

Referring now to FIG. 3, the control system of a CT imaging system suitable for use with the present invention has gantry associated control modules 48 which include: x-ray control 54 which provides power and timing signals to the x-ray source 10, gantry motor controller 56 which controls the rotational speed and position of the gantry 16 and provides information to computer 60, and data acquisition system 62, regarding gantry position, and image reconstructor 68 which receives sample and digitized signals from the detector array 18 via the data acquisition system 62 to perform high speed image reconstruction according to methods known in the art. Each of the above can be connected to its associated elements on the gantry 16 via slip rings 50 and serves to interface computer 60 to various gantry functions.

The speed and position of table 22 along the z-axis, is communicated to and controlled by computer 60 by means of table motor controller 52. The computer 60 receives commands and scanning parameters via operator console 64 which is generally a CRT display and keyboard which allows the operator to enter parameters for the scan and to display the reconstructed image and other information from the computer 60. A mass storage device 66 provides a means for storing operating programs for the CT imaging system, as well as image data for future reference by the operator.

Each data element of a projection set acquired with the above described fan beam tomographic system may be identified by the angles $\theta$ and $\phi$. Referring to FIG. 4(a), the angle $\phi$, is measured from the centermost ray 20 of the fan beam 24, shown in FIG. 1, and identifies a ray 21 within the fan beam 24 and its associated detector 26. $\phi$ will be termed the fan beam angle. $\phi$ is the angular position of the gantry 16 (shown in FIG. 1) and is arbitrarily referenced to zero when the fan beam's center most ray 20 is vertical and directed downward. The distance between the source 10 and the center of rotation of the gantry 16 is termed D and will be referred to below.

In conventional CT imaging, 360° of projection data, termed a projection set, is acquired and reconstructed into a slice image. As shown in FIG. 5(a), the data for a projection set 70 fills a rectangular area in a Cartesian "fan beam" space having a vertical axis measuring argument $\theta$ and a horizontal axis measuring argument $\phi$. Horizontal lines of constant $\theta$ represent single projections taken at gantry position $\theta$ and includes detector signals from angles $\phi$: $-\phi_{max} < \phi < +\phi_{max}$. The gantry angle $\theta$ of the lowest most projection is arbitrarily assigned to 0 and is the first projection of the projection set 70. Successive projections are acquired at increasing gantry angles $\theta$ up to $\theta = 2\pi$ radians while the table 22 is advanced along the z-axis, per helical scanning techniques discussed above.

The projection set 70 is acquired in two stages: first, the gantry angle is advance from 0 to $\pi$ to acquire a first partial fan beam projection set 72. At the conclusion of this acquisition, the slice plane 14 of the imaged object 12 (shown in FIG. 1) has been aligned with the imaging plane. A second partial fan beam projection set 74 is then initiated starting at gantry angle $\theta = \pi$ and continuing to gantry angle $\theta = 2\pi$. The complete fan beam projection set 70 of $2\pi$ radians may be converted into an image by fan beam reconstruction techniques known in the art.

For computational efficiency, the first and second partial fan beam projection sets 72 and 74 may be rebinned to "parallel beam" projections. Such rebinning is described in U.S. Pat. No. 4,852,132 entitled "Method of Collecting Data for X-ray Tomograph" and hereby incorporated by reference. As the name implies, a parallel beam projection is one in which each projection has only parallel rays.

Referring to FIG. 4(b), such a projection set would be obtained by a source 10' and detector 26'. The data elements of a parallel projection set may be identified by the variables $\beta$ and t. The distance t, measured from the centermost ray 20' of the parallel beam 24', identifies each ray 21' of the parallel beam 24' and its associated detector 26' and will be termed the parallel beam offset. $\beta$ is the angular position of the gantry 16 (not shown) and defines the angle of each of the rays 21' and like $\theta$ of the fan beam system, is arbitrarily referenced to zero when the parallel beam's center most ray 20' is vertical and directed downward.

In creating a parallel beam projection set from a fan beam projection set 70, each ray 21 of the fan beam projections of FIG. 5(a) is separated and sorted into new parallel projections. The sorting is governed by the following relationship between the projection data acquired by a fan beam system and the projection data acquired by a parallel beam system. For any two data elements $P_1$ and $P_2$ of a fan beam projection set and a parallel beam projection set respectively:

$$P_1(\theta, \phi) = P_2(\beta, t) \tag{1}$$

if $$\beta = \theta + \phi, \text{ and} \tag{2}$$

$$t = D \sin(\phi) \quad (3)$$

For mathematical convenience, the following substitution will be made:

$$\gamma = \arcsin(t/d) \quad (4)$$

so that $$P_1(\theta, \phi) = P_2(\beta, \gamma) \quad (5)$$

if:

$$\beta = \theta + \phi \text{ and} \quad (6)$$

$$\gamma = \phi \quad (7)$$

The process of rebinning the fan beam projection set 70 of 5(a) yields a parallel beam projection set 76 as shown in the Cartesian "parallel beam" space of FIG. 5(b), having vertical axis measuring $\beta$ and a horizontal axis measuring $\gamma$ as defined above.

The correction of skew artifacts may be performed on the rebinned parallel beam projections of FIG. 5(a) prior to image reconstruction by identifying two projection sets near the slice plane and interpolating and extrapolating a new projection set with reduced helical offset.

The projections sets used for this interpolation and extrapolation need not be a complete 360° of scanned data. A parallel beam projection set having as little as 180° of projection data may be reconstructed into an image and hence used for the extrapolation and interpolation process. Such a reduced projection set will be termed a "half scan"

The fact that an entire slice image may be reconstructed from a half scan follows from the redundancy of data within a full parallel beam projection set of 360°. The source of this redundancy is apparent from inspection of FIG. 4(b). For non-helical scanning, that is where the imaged object 12 does not move during the scanning. the rays 24 within any projection at gantry angle $\beta$ will be exactly 180° opposed to the rays 21 of a projection acquired at a gantry angle $\beta + \pi$ radians. As the attenuation of a ray 21 by the imaged object 12 is indifferent to the direction of the ray 21, the data element obtained for two coincident but opposed rays 21 will be the same, and the projection data for these two gantry angles will be the same, although the order of the data will be reversed. More precisely, for any two data elements $P_a$ and $P_b$:

$$P_a(\beta, \gamma) = P_b(\beta + \pi, -\gamma) \quad (8)$$

In helical scanning, this relationship does not hold exactly. The imaged object 12 moves with rotation of the gantry 16 and hence the projection data obtained for two rays 21 of opposing angle will differ. Nevertheless, the relation (8) above describes pairs of data elements between projections that may be expected to be more highly correlated than other pairs of data elements. The relationship of equation (8) for data obtained from helical scanning will be termed "redundancy".

For parallel projections, therefore, a half scan requires $\pi$ projections of data and two half scans may be obtained in $2\pi$ parallel beam projections.

Referring again to parallel beam space of FIG. 5(b), it may be seen that $2\pi$ of complete parallel beam projection data is not available from the data rebinned from fan beam projection set 70 of FIG. 5(a). Specifically, the areas 82 where $2\pi + \gamma < \beta < 2\pi$ and 84 where $0 < \beta < \gamma$ represent missing portions of projections for certain angles $\beta$.

Accordingly, in order to obtain two half scans of parallel beam data for interpolation, data must be "spliced" into these areas 82 and 84 from elsewhere in the parallel beam space. Such data is preferably related to the missing data of regions 82 and 84 by the redundancy equation (8) above. Also, it is preferable for signal-to-noise ratio considerations to splice data from areas that would otherwise be unused in the reconstruction process. Regions 86 where $2\pi < \beta < 2\pi + \gamma$ and 88 where $\gamma < \beta < 0$ satisfy these requirements. Accordingly, the data of region 88 is spliced into region 82 and the data of region 86 is spliced into region 84 according to the relationship of equation (8).

Two half scans may now be constructed one from the parallel projection set 76: a first half scan from data in the range $0 < \beta < \pi$ and a second half scan from data in the range from $\pi < \beta < 2\pi$. These two half scans may be then interpolated and extrapolated to the slice plane by weighting them accordingly and summing them together. Or, alternatively, and more efficiently, the weights may be applied and the summing carried out by the implicit summation of image reconstruction process as is understood in the art.

The interpolation and extrapolation weights required for each data element in the spliced parallel beam projection set will depend on the data element's distance from the slice plane relative to the distance from the slice plane of its corresponding redundant data element per equation (8) above. The weighting is accomplished by multiplying the values of the redundant data elements by their respective weights.

Specifically, for any two redundant data elements $P_1(\beta, \gamma)$ at $z_1$ and $P_2(\beta, \gamma)$ at $z_2$, the weight $w_1$ for point $P_1$ for linear interpolation or extrapolation to a slice plane at $z_{sp}$ is:

$$w_2 = \frac{z_{sp} - z_1}{z_2 - z_1} \quad (9)$$

and for data element $P_2$ the weight $w_2$ is:

$$w_1 = 1 - w_2 \quad (10)$$

Figures 6A, 6B:
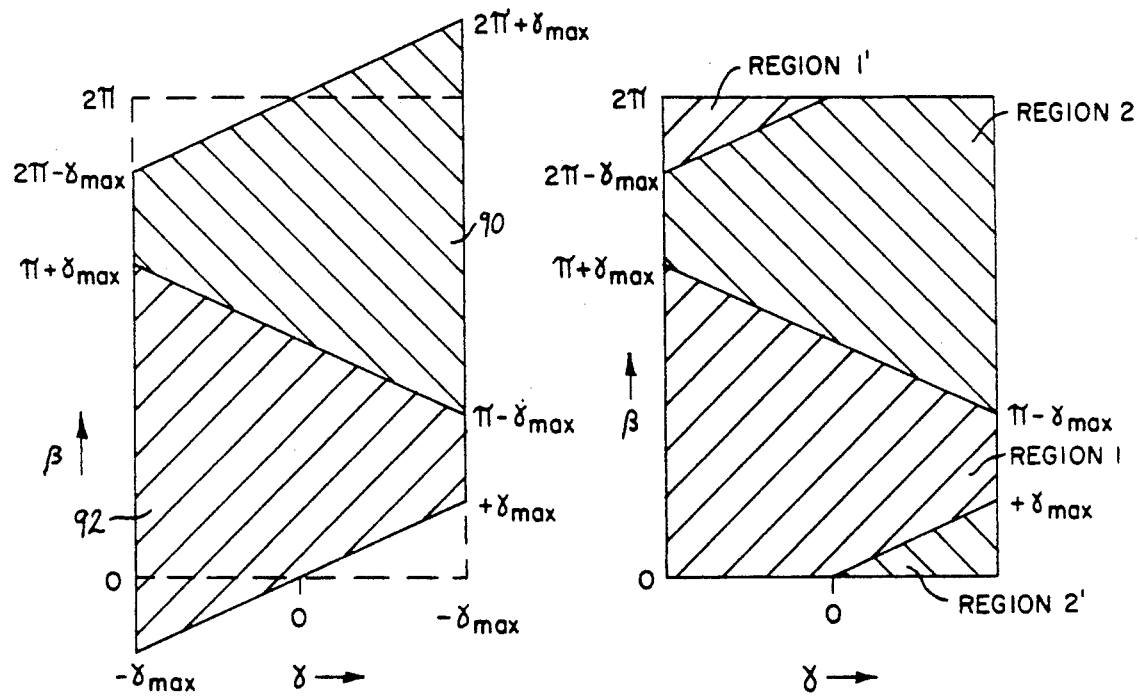
FIG. 6(a) is a graphical representation similar to that of FIG. 5(b) showing the redundant data within the rebinned projection set.
FIG. 6(b) is a graphical representation similar to that of FIG. 5(b) and 6(a) showing the rebinned parallel beam projection set with spliced data to create two parallel beam half scans.

Calculation of these weights requires that the redundant data elements within the parallel beam projection set 76 be determined. Referring to FIG. 6(a), the original parallel beam data 76 rebinned from fan beam data 70 has been divided into sets 90 for $\beta > \pi + \gamma$ and 92 for $\beta > \pi + \gamma$ per equation (8). Regions 90 and 92 identify sets of redundant data and therefore will require separate weighting functions per equation (9) and (10) above. Further, the splicing operation displaces some of the data elements of sets 92 and 90, creating additional regions of dislocated data that require additional unique weighting functions that account for the dislocation.

Therefore, referring to FIG. 6(b), the result of the splicing operation creates four regions each which will require a different weight.

| Region | Boundaries |
| --- | --- |
| 1 | $\gamma < \beta < \pi - \gamma$ |
| 2 | $\pi - \gamma < \beta < 2\pi + \gamma$ |
| 1' | $\beta > 2\pi + \gamma$ |

-continued

| Region | Boundaries |
| --- | --- |
| 2' | $\beta < \gamma$ |

Regions 1' and 2' reflecting their origins as portions of set 80 and 78 now identified as region 1 and 2 in FIG. 6(b).

With regions of corresponding redundant data elements identified, the z values of the data elements of those regions must be determined. The z value of each data element is proportional to the value of $\theta$ for the corresponding data element of the fan beam projection set. Therefore:

$$z(\beta, \gamma) = k(\theta) \quad (11)$$
$$= k(\beta - \gamma) \text{ per equation (7) and (8)} \quad (12)$$

The z value of the slice plane is $k(\pi)$ as defined previously.

The weighting function $w_1(\beta, \gamma)$ for region 1 may be now readily determined.

$$w_1 = \frac{1}{2} + \frac{\beta - \frac{\pi}{2}}{\pi + 2\gamma} \quad (13)$$

Similarly, for region 2 the weighting factor is:

$$w_2 = \frac{1}{2} - \frac{\beta - \frac{3\pi}{2}}{\pi - 2\gamma} \quad (14)$$

The weighting factor for region 1' is the same as that for region 1 but shifted by $2\pi$ as a result of the splicing procedure. Hence:

$$w_{1'} = \frac{1}{2} + \frac{\beta - \frac{5\pi}{2}}{\pi + 2\gamma} \quad (15)$$

And for region 2', $w_{2'}$ is:

$$w_{2'} = \frac{1}{2} - \frac{\beta + \frac{\pi}{2}}{\pi - 2\gamma} \quad (16)$$

The boundaries between the regions 1, 1', 2, and 2' will have discontinuities as a result of the discontinuities in the weighting factors used for the interpolation of the data described above. These discontinuities may create streak image artifacts in the final image. The discontinuity may be eliminated by feathering $w_1$, $w_{1'}$, $w_2$ and $w_{2'}$ near the interfaces of their regions. The feathering is performed over an area between the regions of height $\omega$. A value of $\omega$ equivalent to the angle subtended by ten detector elements 26 is found to be sufficient.

Specifically, $w_1$, $w_{1'}$, $w_2$, and $w_{2'}$ are multiplied by respective feathering functions $f_1(\beta, \gamma)$, $f_{1'}(\beta, \gamma)$, $f_2(\beta, \gamma)$, $f_{2'}(\beta, \gamma)$ and the product applied to the data of the entire projection set where:

$$f_1(\beta, \gamma) = \begin{cases} 3x^2(\beta) - 2x^3(\beta) & \text{for } \gamma - \omega/2 \leq \beta \leq \gamma + \omega/2 \\ 1 - 3x^2(\beta') - 2x^3(\beta') & \text{for } -\gamma + \pi - \omega/2 \leq \beta \leq -\gamma + \pi + \omega/2 \\ 1 & \text{for } \pi - \gamma - \omega/2 > \beta > \gamma + \omega/2 \\ 0 & \text{elsewhere} \end{cases} \quad (17)$$

for $$x(\beta) = \frac{\gamma - \beta}{\omega} + .5 \quad (18)$$

and $$x(\beta') = \frac{\beta + \gamma + \pi}{\omega} + .5 \quad (19)$$

and $$f_2(\beta, \gamma) = \begin{cases} 3x^2(\beta) - 2x^3(\beta) & \text{for } \pi - \gamma - \omega/2 \leq \beta \leq \pi - \gamma + \omega/2 \\ 1 - 3x^2(\beta') - 2x^3(\beta') & \text{for } 2\pi + \gamma - \omega/2 \leq \beta \leq 2\pi + \gamma + \omega/2 \\ 1 & \text{for } \pi - \gamma + \omega/2 < \beta < 2\pi + \gamma - \omega/2 \\ 0 & \text{elsewhere} \end{cases} \quad (20)$$

where $$x(\beta) = \frac{\beta + \gamma - \pi}{\omega} + .5 \quad (21)$$

and $$x(\beta') = \frac{-\beta + \gamma + 2\pi}{\omega} + .5 \quad (22)$$

and $$f_1(\beta, \gamma) = \begin{cases} 0 & \text{for } 2\pi + \gamma - \omega/2 > \beta \\ 3x^2(\beta) - 2x^3(\beta) & \text{for } 2\pi + \gamma - \omega/2 \leq \beta \leq 2\pi + \gamma + \omega/2 \\ 1 & \text{for } \beta > 2\pi + \gamma + \omega/2 \end{cases} \quad (23)$$

where $$x(\beta) = \frac{-\beta + \gamma + 2\pi}{\omega} + .5 \quad (24)$$

$$f_2(\beta, \gamma) = \begin{cases} 0 & \text{for } \gamma + \omega/2 < \beta \\ 3x^2(\beta) - 2x^3(\beta) & \text{for } \gamma - \omega/2 \leq \beta \leq \gamma + \omega/2 \\ 1 & \text{for } \beta < \gamma - \omega/2 \end{cases} \quad (25)$$

where $$x(\beta) = \frac{\gamma - \beta}{\omega} + .5 \quad (26)$$

Many modifications and variations of the preferred embodiment which will still be within the spirit and scope of the invention will be apparent to those with ordinary skill in the art. For example, other interpolation methods than linear interpolation may be used including those using data from additional half scans before and after the first and second half scans and using higher order interpolation methods. Further, other feathering functions such as those with linear relationships could be used.

We claim:

1. A method of producing a tomographic image of an imaged object from data acquired in a helical scan, the data acquired as a series of fan beam projections at a plurality of gantry angles $\theta$ about a z-axis and within an image plane, the fan beam projection including a plurality of data at fan beam angles $\phi$, comprising the steps of:

a) identifying a slice plane $z_{sp}$ relative to the imaged object and parallel to the image plane;
   b) acquiring a fan beam projection set of data over $2\pi$ of source rotation;
   c) moving the imaged object along the z-axis and rotating the source so that imaging plane crosses the slice plane during the acquisition of a fan beam projection set;
   d) rebinning the fan beam projection set into parallel beam projections having parallel beam gantry angles $\beta$ and fan beam offsets including redundant and missing data relative to a complete parallel beam projection set over $2\pi$ of parallel beam gantry angles;
   e) dividing the parallel beam projection set into two half-scans;
   f) splicing data between the half-scans by using the redundant data of one half scan as the missing data of the other half scan to create a complete parallel beam projection set over $2\pi$ of parallel beam gantry angles, the splicing being effected by changing at least the gantry angle $\beta$ of the redundant data;
   g) extrapolating and interpolating the data of the half-scans to a slice plane parallel beam projection set; and
   h) reconstructing the slice plane parallel beam projection set into a slice image.

2. The method of claim 1 where the data of the half-scans is extrapolated and interpolated by applying a weighting function to the half-scans and reconstructing the half-scans as weighted into a slice image per step (h).

3. The method of claim 2 wherein the weighting function for pairs of redundant data within each half-scan add to a constant and the weight for any such redundant datum is a function of $\theta$.

4. The method of claim 1 including the step of applying a feathering weighting to the half scans.

5. The method of claim 1 where the slice plane crosses the imaging plane midway through the acquisition of the fan beam projection set.

* * * * *

UNITED STATES PATENT AND TRADEMARK OFFICE
CERTIFICATE OF CORRECTION

PATENT NO. : 5,216,601
DATED : June 1, 1993
INVENTOR(S) : Crawford et al.

It is certified that error appears in the above-identified patent and that said Letters Patent is hereby corrected as shown below:

Col. 5, line 68  "$\phi$ is the angular" should be
-- $\theta$ is the angular --.

Col. 8, line 53  "$\beta > \pi + y$" should be -- $\beta < \pi + y$ --.

Signed and Sealed this

Fourth Day of January, 1994

Attest:

BRUCE LEHMAN

Attesting Officer       Commissioner of Patents and Trademarks